United States Patent [19]

Van Dyke et al.

[11] Patent Number: 4,494,554
[45] Date of Patent: Jan. 22, 1985

[54] SKIN TEST DEVICE USING I.C. COMPARATOR CIRCUIT

[75] Inventors: Helga M. Van Dyke, 469 Wellington Rd., Orange, Calif. 92669; Rudolph C. DeGroot, Sr., Laguna Niguel, Calif.

[73] Assignee: Helga M. Van Dyke, Orange, Calif.

[21] Appl. No.: 305,547

[22] Filed: Sep. 25, 1981

[51] Int. Cl.³ .............................................. A61B 5/05
[52] U.S. Cl. .................................. 128/734; 324/65 R
[58] Field of Search .............................. 128/734–735, 128/630, 693; 324/65 R

[56] References Cited

U.S. PATENT DOCUMENTS

| | | | |
|---|---|---|---|
| 3,207,151 | 9/1965 | Takagi | 128/734 |
| 3,834,374 | 9/1974 | Ensanian | 128/734 X |
| 3,859,594 | 1/1975 | Grindheim | 324/65 R X |
| 3,924,606 | 12/1975 | Silva et al. | 128/734 |
| 3,949,736 | 4/1976 | Vrana et al. | 128/734 |
| 3,960,010 | 6/1976 | Gustafsson | 324/65 R |
| 3,978,849 | 9/1976 | Geneen | 128/690 |
| 4,088,125 | 5/1978 | Forgione et al. | 128/734 |
| 4,096,852 | 6/1978 | Adams | 128/734 |
| 4,331,160 | 5/1982 | Zito, Sr. | 128/734 |

FOREIGN PATENT DOCUMENTS 2508742  9/1976  Fed. Rep. of Germany ...... 128/735

Primary Examiner—Lee S. Cohen
Assistant Examiner—Angela D. Sykes
Attorney, Agent, or Firm—Willie Krawitz

[57] ABSTRACT

A skin condition tester is disclosed employing an inexpensive, battery powered, I.C. comparator circuit that tests for dry, normal and oily skin. An instantaneous digital readout is obtained that may be converted into a light or a meter reading.

The circuit is lightweight and small, with no moving parts, and when used in conjunction with LEDs, provides virtually an instantaneous reading. The device is readily adapted to obtain a number of readings from an individual, without the necessity of dial adjustments.

4 Claims, 1 Drawing Figure

SKIN TEST DEVICE USING I.C. COMPARATOR CIRCUIT

BACKGROUND OF THE INVENTION

This invention relates to a new and improved tester for skin dryness employing an inexpensive, battery driven, I.C. comparator bridge circuit. An instantaneous, digital readout is obtained that is converted into a light readout using say, LEDs, or into a meter reading.

Various skin condition testing devices have been developed, but are usually bulky, cumbersome and quite expensive. Many of these devices require line wire power, and the possibility of an electric shock tends to deter potential users from being tested. Consequently, the use of these testing devices has been limited. Basically, a testing device is desired that requires few circuit components which are expensive and is lightweight; also, the device should operate at low power. Preferably, the testing device should not require adjustable settings or moving parts, and is readily portable.

Use of a battery powered device is inherently much safer than one powered by A.C. and would obviate the need for obtaining a design and circuit approval from one or more testing laboratories. There is also desired a skin testing device having a fast response time with repeatable results.

THE INVENTION

According to the invention, there is provided a battery driven, skin testing device, comprising a bridge circuit including I.C. comparators that have preset circuit resistances to enable a serial change of state when the circuit resistances equal skin or scalp resistances corresponding to dry, normal and oily conditions. A touch plate is employed as a ground terminal on the user, and a probe is used to complete the connection on that portion of the user's body where the skin condition is to be tested. Thus, the skin to be tested forms one arm of a bridge circuit, the other arms including the I.C. comparator, preset resistances and readout LEDs.

Typical resistance ranges that will activate a comparator and corresponding LEDs are about 15K–18K for oily skin, about 15K–17K for normal skin, and about 12K–15K serially for dry skin. The total maximum resistance should not exceed about 55K. The circuitry only requires a battery strength of about 5–12 volts, using say a single 9 volt battery.

BRIEF DESCRIPTION OF THE DRAWINGS

The single FIGURE illustrates the circuit diagram for the skin condition probe of this invention.

DESCRIPTION OF THE PREFERRED EMBODIMENTS

Figure 1:
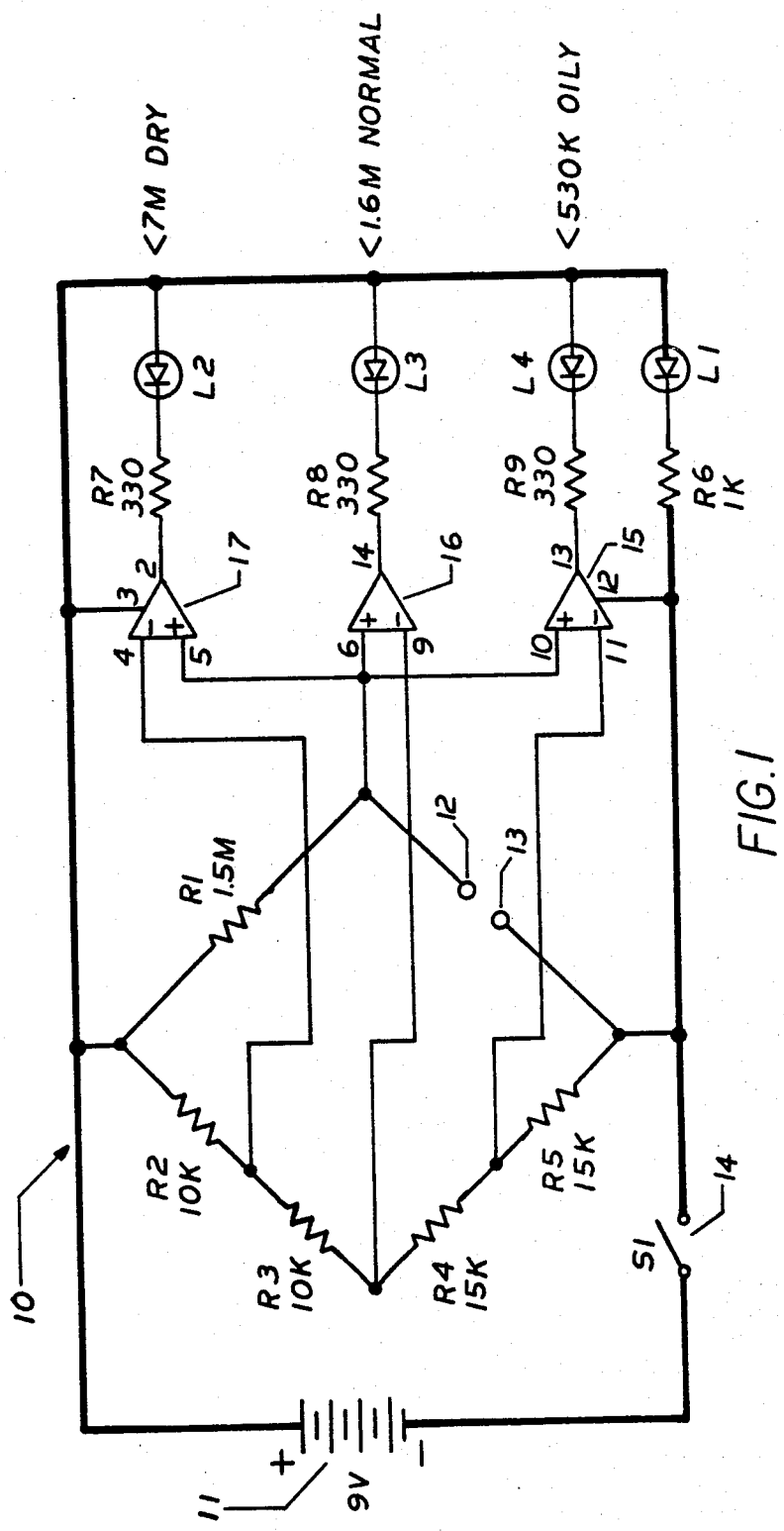

The skin test device circuit 10 of this invention is shown in the drawing, and includes a battery 11, probe 12 and a touch plate 13 connected through a switch 14 to the battery. A quad comparator (LM 339) is connected internally to produce three units 15, 16 and 17, and these are connected on their positive, non inverting sides to the probe and to the battery through a resistance R1. Together with the skin resistance elements in the circuit, R1 presets the resistance levels for changing the state of a comparator when the skin resistance equals the preset resistance. The probe 12 is manufactured of a good quality brass, and is impedance matched to the circuit. The negative sides of the comparators 15, 16 and 17 are connected through resistances R3, R4 and R5 to the battery negative. Resistances R2 and R6 are used to reduce battery drain, and the preferred maximum of the resistances R2, R3, R4 and R5 is about 55K.

LEDs L1, L2, L3 and L4, and corresponding series resistances R6, R7, R8 and R9 are respectively activated when the skin or scalp resistance falls into the values defined by R5, R4+R5, and R3+R4+R5. When the switch 14 is closed, L which is the 'on' light, will turn on prior to testing and will remain on during the test. If the user's skin or scalp condition is oily, the lowest resistance in the bridge circuit, R5, will equal the skin resistance; this will change the state of the comparator and turn on L4. If the user's skin is of normal dryness, the skin resistance will equal R4+R5, and this will similarly change the state of the comparator 16 and turn on LED 3, while LED 4 still remains on. If the user's skin is drier than normal, R3+R4+R5 will equal the dry skin resistance, and this will change the state of comparator 17 and turn on LED 2; LEDs 3 and 4 will still remain on.

If a skin resistance falls on, or close to the borderline between resistances defining a particular skin type, the best interpretation is to select the reading that first appears. Since a skin condition reading can be obtained quickly, it is quite easy to determine whether a borderline condition varies from, say dry to normal, and normal to oily. Thus for example, if the initial readings test predominantly 'dry', and then change to 'normal', the skin is treated as 'dry', tending to 'normal'. On the other hand, if the initial skin readings test 'normal', and then change to 'dry', the skin is treated as 'normal', tending to 'dry'.

The skin testing device of this invention requires few and small size circuit components, and this results in a small, lightweight package. Including the container, the testing device weighs about 8 ounces and has an overall size of about 11 cm.×6½ cm.×3 cm. No resistance or other settings are needed during use to obtain a reading. Together with the almost instantaneous response reading and its small, lightweight features, use of the skin testing device of this invention is greatly facilitated.

Obviously, other equivalents of this invention are possible without departing from the spirit thereof. Also, the resistance ranges of the comparators when changing state may be varied from those disclosed; this would depend mainly on the results of testing large numbers of individuals.

We claim:

1. A portable device for testing skin or scalp resistance to determine an oily, normal and dry skin condition, comprising:
   a. a battery driven bridge circuit providing preset, fixed resistances in a first set of adjacent legs of the bridge circuit;
   b. a skin surface probe-touchplate and battery drain resistance in a second set of adjacent legs of the bridge circuit opposed to the first set of legs, the probe-touchplate being adapted to test an area of skin for resistance corresponding to the skin condition;
   c. a plurality of I.C. comparators connected in the bridge circuit adapted to turn on and off when comparing with a skin resistance that is equivalent to oily, normal and dry of respectively about: 15K–18K; 30K–35K; and, 42K–50K ohms corresponding to the fixed resistances in the first set of legs of the bridge circuit;
d. light indicators associated with each of the comparators for instantaneous actuation when the associated comparator changes state; and,
e. biasing resistances associated between each comparator and its associated light indicator;

the battery voltage for driving the bridge circuit, comparators and light indicators being about 5-12 volts; whereby: i. the light indicators serially activate when the comparators change state upon equalling the resistance associated with a particular skin condition; and, ii. when a skin resistance occurs between resistances defining the particular skin condition, thereby activating two light indicators, a selection is made based primarily on which light indicator is initially actuated, and secondarily on which light indicator is subsequently actuated.

2. The skin testing device of claim 1, in which each comparator is a quad comparator, and the indicators are light emitting diodes.

3. The skin testing device of claim 1, in which the probe is brass, and is impedance matched to the bridge circuit.

4. The skin testing device of claim 1, in which the combined maximum preset resistance for the comparators and the battery drain resistance is about 55K ohms.

* * * * *